United States Patent [19]
Reed et al.

[11] Patent Number: 5,815,264
[45] Date of Patent: Sep. 29, 1998

[54] SYSTEM FOR ACQUIRING AN IMAGE OF A MULTI-PHASE FLUID BY MEASURING BACKSCATTERED LIGHT

[75] Inventors: Barry W. Reed, Auburn; Jon V. Hokanson, Redmond; Oliver S. Hamann, Redmond; Thomas W. Montague, Redmond, all of Wash.

[73] Assignee: Laser Sensor Technology, Inc, Redmond, Wash.

[21] Appl. No.: 835,188

[22] Filed: Apr. 7, 1997

Related U.S. Application Data

[63] Continuation-in-part of Ser. No. 310,630, Sep. 21, 1994, Pat. No. 5,619,043.
[51] Int. Cl.$^6$ ................................................. G01N 21/49
[52] U.S. Cl. .......................... 356/336; 250/574; 356/342; 356/343
[58] Field of Search .................... 356/336, 338, 356/342, 343; 250/574

[56] References Cited

U.S. PATENT DOCUMENTS

| | | |
|---|---|---|
| 4,140,395 | 2/1979 | Kreikebaum ............................ 250/574 |
| 4,776,697 | 10/1988 | Kamrat . |
| 5,153,674 | 10/1992 | Böbel et al. ............................ 356/336 |
| 5,159,403 | 10/1992 | Kosaka . |
| 5,247,339 | 9/1993 | Ogino . |
| 5,272,354 | 12/1993 | Kosaka . |
| 5,561,517 | 10/1996 | Horiuchi et al. . |
| 5,594,544 | 1/1997 | Horiuchi et al. . |

*Primary Examiner*—Richard A. Rosenberger
*Attorney, Agent, or Firm*—Christensen, O'Connor, Johnson & Kindness PLLC

[57] ABSTRACT

An in-situ imaging system suitable for analyzing particles or droplets contained in process reactor vessels or pipelines at full process concentrations is disclosed. The system includes a light source capable of high peak power output operated in a pulsed mode that is located inside of a probe. The light from the light source is coupled into an optical fiber. The light is carried by the optical fiber to a lens system near the end of the probe which focuses the light through a window to the area which coincides with the field of view in the focal plane of the imaging optics. The imaging optics collect the light which is back-scattered from particles or droplets, magnifying the image and projecting it onto an image detector such as a CCD array.

11 Claims, 9 Drawing Sheets

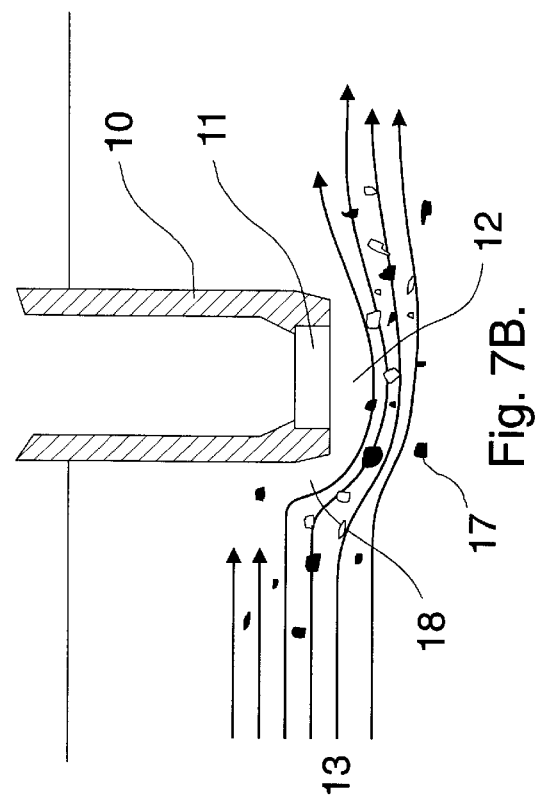
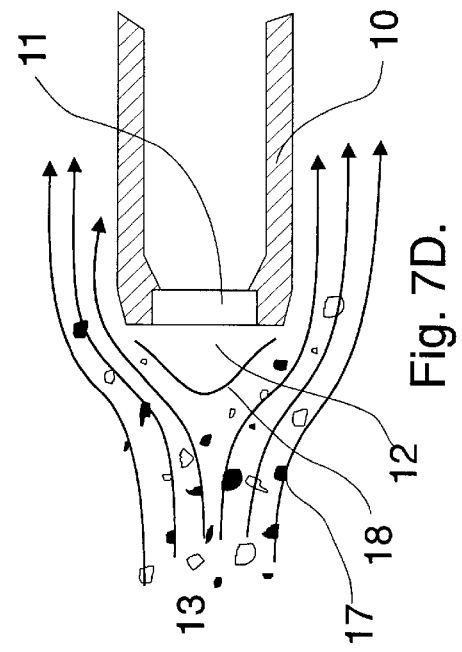
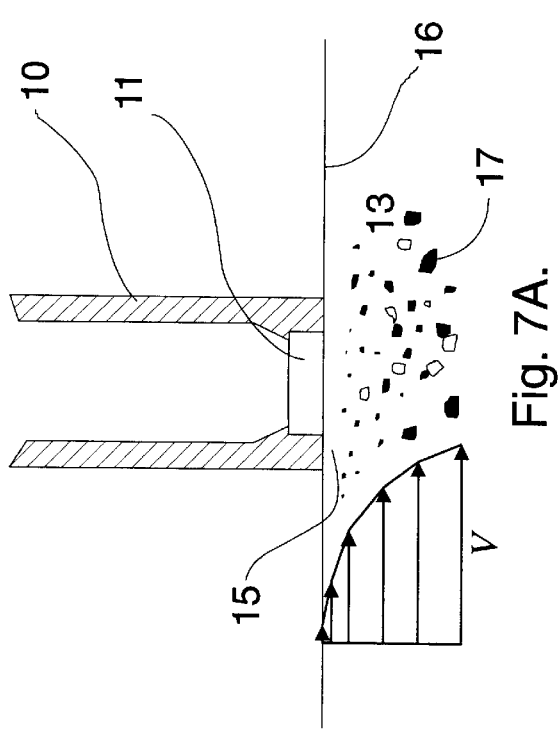
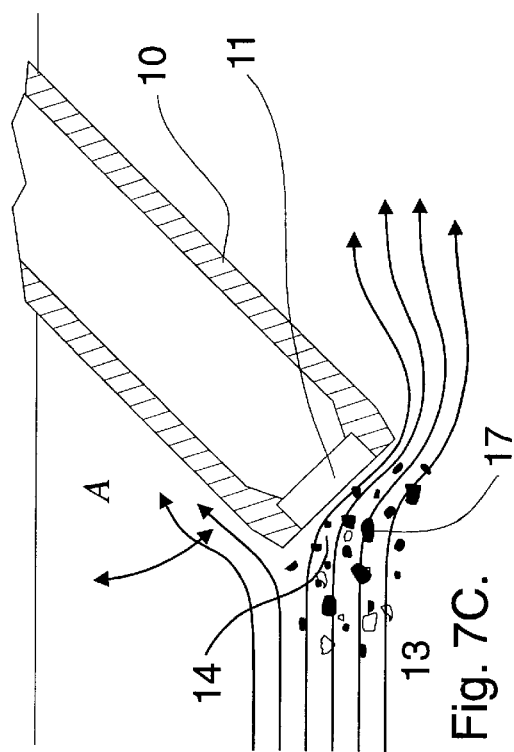

SYSTEM FOR ACQUIRING AN IMAGE OF A MULTI-PHASE FLUID BY MEASURING BACKSCATTERED LIGHT

FIELD OF THE INVENTION

This is a continuation-in-part of U.S. patent application Ser. No. 08/310,630 entitled "A System for Acquiring an Image of a Multi-Phase Fluid by Measuring Backscattered Light" filed Sep. 21, 1994, now U.S. Pat. No. 5,619,043, assigned to the same assignee herein, and incorporated by reference in its entirety.

TECHNICAL FIELD OF THE INVENTION

The present invention relates to an apparatus and method for analyzing the physical characteristics of a multi-phase fluid medium by imaging, the characteristics including shape, size and concentration.

BACKGROUND OF THE INVENTION

There are many applications where particle characterization measurements can provide for improved process control, leading to increased throughput, higher recovery rates, reduced reagent consumption, and better product quality. These benefits result in reduced cost and increased profits, strong justifications for the use of process control instrumentation. However, although there are instruments available for measuring particle size, many processes operate at high particle concentrations that are out of the measuring range for most of these devices. Thus, there is a lack of particle measurement instrumentation that can be used in-situ for real-time measurements that are necessary for process control.

In a typical process, such as a polymerization or crystallization reaction, particles or droplets are suspended in a flowing medium, liquid or gaseous, while chemical or physical changes are taking place to the materials in the slurry. In many cases these changes are very dynamic, and thus the materials cannot be measured when removed from the pipeline or vessel. For instance, if a sample is obtained from a crystallization vessel, the crystals will continue to grow or dissolve while the sample is transported to a measuring instrument. Droplet dispersions will coalesce quickly when they are removed from their agitated environment, preventing any attempt to make accurate off-line measurement.

Optical methods have many advantages for particle sizing, but also have one serious limitation. At high particle concentrations, light is scattered from particle to particle, and such so-called multiple scattering are highly unpredictable, depending on factors like the refractive index of the materials, surface roughness, transparency, size, shape, etc. Optical measurement methods lose precision and resolution at high concentrations of particles, because the equations which relate particle size to the measurement all assume negligible attenuation of the light, or scattering by only one particle. Imaging of particles at high concentrations is affected in the same way; multiple scattering reduces contrast and decreases the ability to resolve particles, especially small particles or surface features.

U.S. Pat. No. 4,871,251 describes an optical device which can measure particles in high concentration slurries. It does so by scanning a focused laser across the particles and measuring the time that a particle is in the beam, it produces a statistical information related to only one dimension of the particles, but cannot distinguish shape, and does not measure size absolutely. This method gains the ability to work at high concentrations by the use of a focused beam, but the trade-off is that it cannot make precise individual measurements of size or shape. It relies on high speed and statistical accuracy instead.

There are many other methods to measure particle size "off-line" in the laboratory, including sieving, sedimentation, electrozone, numerous optical scattering techniques, acoustics and imaging. All of these methods, except imaging, can only produce a single particle dimension, such as particle volume or diameter. Imaging can show size, shape, surface features, clarity, and other physical characteristics of a particle.

Imaging is therefore is the only known method of accurately measuring the size and shape of individual particles, but this is usually done off-line, under a microscope. Obviously, an in-situ, real-time imaging system would have great value in the process industries. There have been some attempts at making in-situ imaging devices, but all have disadvantages that the present invention overcomes.

Most of these systems utilize a transmission configuration to produce images of sufficient contrast. A system shown in U.S. Pat. No. 4,529,306 has been marketed by Flow Vision, Inc. for the detection of contamination polymer melts in extruders. U.S. Pat. No. 4,075,462 also describes an apparatus for producing an image of particles using a transmission geometry. Another very similar example is shown in U.S. Pat. No. 4,136,950. In all of these devices, the illuminating beam is transmitted through the flowing material towards the detector, which detects the shadows of particles as they pass between the source and detector. Because of the transmission geometry, these can only be used to measure particles at very low concentrations.

U.S. Pat. No. 5,191,388, also assigned to Flow Vision, describes an apparatus using tapered optical fibers to create an enlarged image of particles that are adjacent to the small end of the ordered fiber bundle. This device is limited by several problems: 1) the size resolution can be no smaller than the center to center distance a between the fibers, 2) the same fiber bundle is used for illumination as well as imaging, which means that even with anti-reflective coatings, at least some of the illuminating light is reflected directly back into the imager by each of the fiber end surfaces causing a loss of contrast, 3) tapered fiber bundles can be made to a maximum length of only about 6 inches, limiting the length of the probe, 4) tapered in fiber bundles are inefficient light transmission devices, the transmission through a 10 mm length is only 50–60% through a 10 mm length. At the maximum length of about 6 inches, less than 40% of the light will be transmitted, both in the illuminating direction and in the receiving direction, and 5) image quality also decreases with length, because some light leaks between fibers along the length of the bundle. The longer the bundle, the more crosstalk between fibers is generated, leading to a loss of contrast and image sharpness. Contrast can be improved by adding light-absorbing material between the fibers, but this also creates even higher transmission losses.

Another alternative method is to use a borescope manufactured by one of several companies (such as Schott, Olympus, or Lenox), inserted into a process stream. Such a system is described in detail by Dr. Arthur Boxman (presented as a part of the Short Course titled "Advances in the Measurement and Control of Particle Systems", held on Jul. 9, 1996 at the Engineering Research Center at the University of Florida). The borescope can have a small diameter, and is equipped with optical fibers arranged concentrically around the objective lens to provide illumination from a remote light source. Inserting the borescope into a probe, with a window to isolate the optics from the process stream, Dr. Boxman built an inspection system which was inserted into a process.

Although workable for some applications, this system, too, has disadvantages. The optical fibers provide a diffused light which illuminates a wide area around the field of view, allowing light from outside the target area to be scattered into the field of view, causing a loss of contrast, making resolution of the features of the particles difficult. Another disadvantage is that the borescope optic must be focused by adjusting the eyepiece, which changes the focal length of the system, changing the magnification, and in turn changes not only the apparent size of the imaged particles, but also the position relationship of the light source to the focal point.

The previous devices have several disadvantages in common. The illumination of the material is accomplished by a diverging beam, or a broad beam of nearly collimated light, the theory being that flooding the area with large amounts of light will produce the best images. In cases where there is little material of interest in the field of view, this is true that increasingly large amounts of light will also increase the amount of light received by the imaging optics. When particle concentrations are high, however, excessive amounts of light, more specifically uncontrolled light, will cause multiple scattering of the light in the field of view of the optical system, in turn lowering the contrast of the resulting image. Also, the energy of such a beam is spread out over a wide area, which in turn requires even greater light intensity to provide sufficient back-scattered light.

The prior art also teaches that the mounting of these devices be such that the viewing window is flush with the wall of the pipeline or vessel carrying the slurry to be measured. The present invention illustrates why this concept is not feasible for most applications.

SUMMARY OF THE INVENTION

The present invention is an in-situ imaging system which addresses all of the above requirements, and is suitable for analyzing particles or droplets contained in process reactor vessels or pipelines at full process concentrations. It can capture images of particles, droplets, or other objects suspended in a fluid medium, even at high concentrations, and is capable of resolving features down to a very small size, to approximately the wavelength of the illuminating light. It overcomes the problems of previous in-line imaging systems, in particular those caused by multiple scattering and particle speed, and in addition, it is a system which is contained in a small diameter probe, which can be inserted directly into a process stream with minimal disruption of the flow, while reaching points deep in the stream which are representative of the overall process being measured. It utilizes a fixed focal length optical system, with the additional advantage of being able to move the focal plane relative to a window surface to optimize the image quality.

In one preferred embodiment, the light source is a laser diode, capable of high peak power output, operated in a pulsed (short duration ON periods) mode, and is located inside of the probe. In another embodiment, a laser such as a frequency doubled Nd:Yag or similar, is located outside of the probe in a separate housing. The light from the light source is coupled into an optical fiber. The light is carried by the optical fiber to a lens system near the end of the probe which focuses the light through a window to the area which coincides with the field of view in the focal plane of the imaging optics. The imaging optics collect the light which is back-scattered from particles or droplets, magnifying the image and projecting it onto an image detector such as a CCD array.

The illumination system, imaging optics, and image detector comprise a fixed focus optical system. This optical system may be moved relative to the window in order to locate the focal plane of the system at a location which is optimum for obtaining the best images under the prevailing conditions.

The light source is switched on for very short periods of time (pulsed operation) to illuminate the particles, such periods of time being short enough that a particle carried by the process stream does not move a significant distance during the illuminating pulse. The illumination period is synchronized with the integration period of the image detector.

The output from the image detector is converted to a standard video signal or into a digital data stream, either of which may be converted into images for viewing on a display device, such as a CRT video monitor, or may be further processed by special signal processing means which can extract size, shape, and other information from the images automatically.

The probe tube is inserted through an insertion assembly so that the front viewing window is in direct contact with the material flow, and can be positioned so that the flow will provide a continuous and representative stream of material past the window. Best measuring conditions are obtained by placing the probe window at an angle of approximately 45° to the flow, such that the stream is impinging on the window so that the momentum of the particles will force them against the window surface, allowing them to be viewed by the imaging optics. This provides a better and more representative sample of the material to contact the window, as opposed previous methods of mounting a window flush with the vessel or pipeline wall, or mounting a probe such that the window surface is parallel to the flow path.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 7A–7D show different flow patterns at the tip of a probe placed inside a moving stream;

DETAILED DESCRIPTION OF THE PREFERRED EMBODIMENT

Figure 1:
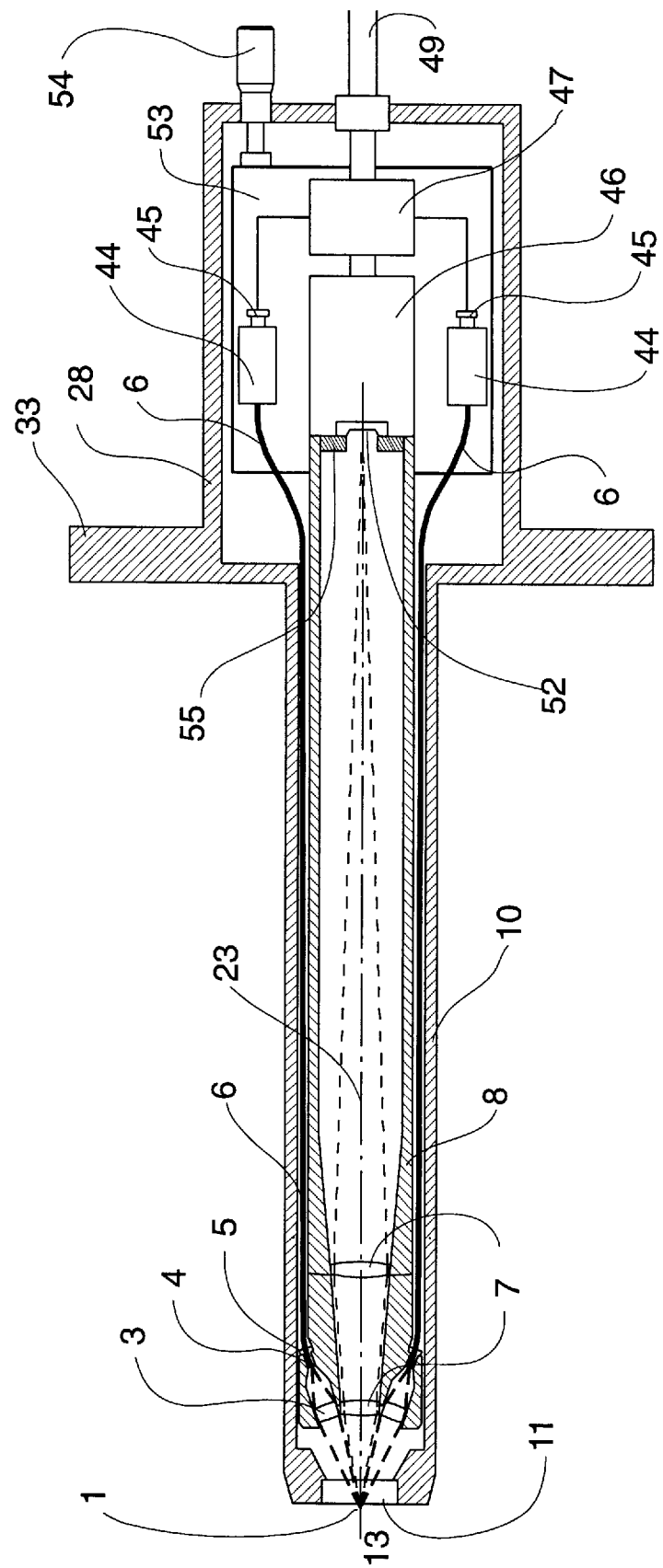
FIG. 1 is a cross section view of the probe, showing the general arrangement of the focusing illumination system and the imaging optics.

FIG. 1 shows the preferred embodiment of the probe assembly in cross section. There are two major sections of the probe assembly: a forward part being a probe tube 10 which is closed at the distal slurry end by a window 11 and a rear part being a probe housing 28 which is generally not inserted in a process flow to be monitored. The probe tube 10 and probe housing 28 are connected to form a rigid sealed shell which contain all of the parts of the probe and protect them from the process environment.

A cable 49 supplies power and control signals to the probe, the cable 49 being connected to the probe housing 28. A high-speed driver circuit 47 generates a short-duration pulse of electrical current to a laser diode 45, causing the laser diode 45 to emit a pulse of light with the same short duration as the current pulse. The light from laser diode 45 is guided into an optical fiber 6 by a coupler 44, and carried by fiber 6 to the end of the fiber at a ferrule 4. Light from the fiber 6 forms a diverging beam according to the numerical aperture of the fiber. Illumination control lens 3 focuses the light to a small beam waist at a focal spot 1, which is located at or near the surface of window 11 which is in contact with the slurry flow 13, to illuminate the particles flowing past the window. The width of the focal spot is controlled by the distance relationship of the end of the ferrule 4 and lens 3. The lateral position of the focal spot with respect to the field of view may be adjusted by displacing the ferrule 4 versus the optical axis of lens 3, which is shown in more detail in FIG. 5.

There may be multiple laser diodes, each having its own driver, coupler, fiber and illuminating control lens. The focal spot 1 is located at the intersection of the optical axis of the imaging optical system and the focal plane of the imaging optical system comprising lens group 7, and image detector 52. Lens group 7 focuses the image plane at focal spot 1 onto an image detector 52. Lens group 7 may also be designed to magnify the image if needed, and may comprise more than one lens element.

In the preferred embodiment, the image detector 52 is a CCD containing a number of elements forming an array. The size of these elements and the magnification of the imaging optical system are factors in the resolving power of the system. For example, 10×10 mm elements and a 10 X magnification, will yield a best resolution of 1 mm in size. There are other optical factors which can limit the resolution of the system, and the optical system must be designed carefully to minimize these effects. There are several CCD devices available which are suitable, such as the TC 241 from Texas Instruments. Electronics package 46 contains conventional circuitry to convert the image on the image detector 52 to a signal which is transmitted by cable 49 to a viewing display or to an image processing system which can determine characteristics, such as shape, size, and number from the images of objects flowing in the slurry 13. Cable 49 also carries power supplies and control signals to the electronics in the probe.

An electronic shutter assembly 55 is used to limit optical noise in cases where the backscattered light is very low. Since the CCD will continue to integrate during period between the illuminating pulses, any stray light striking the image detector surface will cause undesired noise in the image. By "opening" the electronic shutter synchronize with the time period of the illumination pulse, optical noise is minimized. An example of an electronic shutter that can open for very short time periods of less than 1 μsec is a Pockels cell, type LX415 from Cleveland Crystals, Inc.

An optic assembly support 53 holds the laser diode assemblies (44 and 45) as well as the driver electronics 47, and also supports the CCD imager 46 and an optic support tube 8, which contains all of the other optical components. The illumination fibers 6 are fixed to the outside of optic support tube 8. The above parts are all therefore connected as a single assembly, and are housed within the outer probe assembly, comprising probe tube 10 and housing 28. Window 11 is attached at the end of tube 10. A focus screw 54 is fixed to housing 28, with the end attached to the optic support 53, so that by turning focus screw 54, the inner assembly 53 moves in relation to the outer assembly 28. This adjusts the position of focal point 1 with respect to the window 11 so that the distance from the window may be optimized for the best image acquisition for the process conditions. Locking collar 33 provides means to attach the probe to the insertion means which is described later in more detail.

Figure 2:
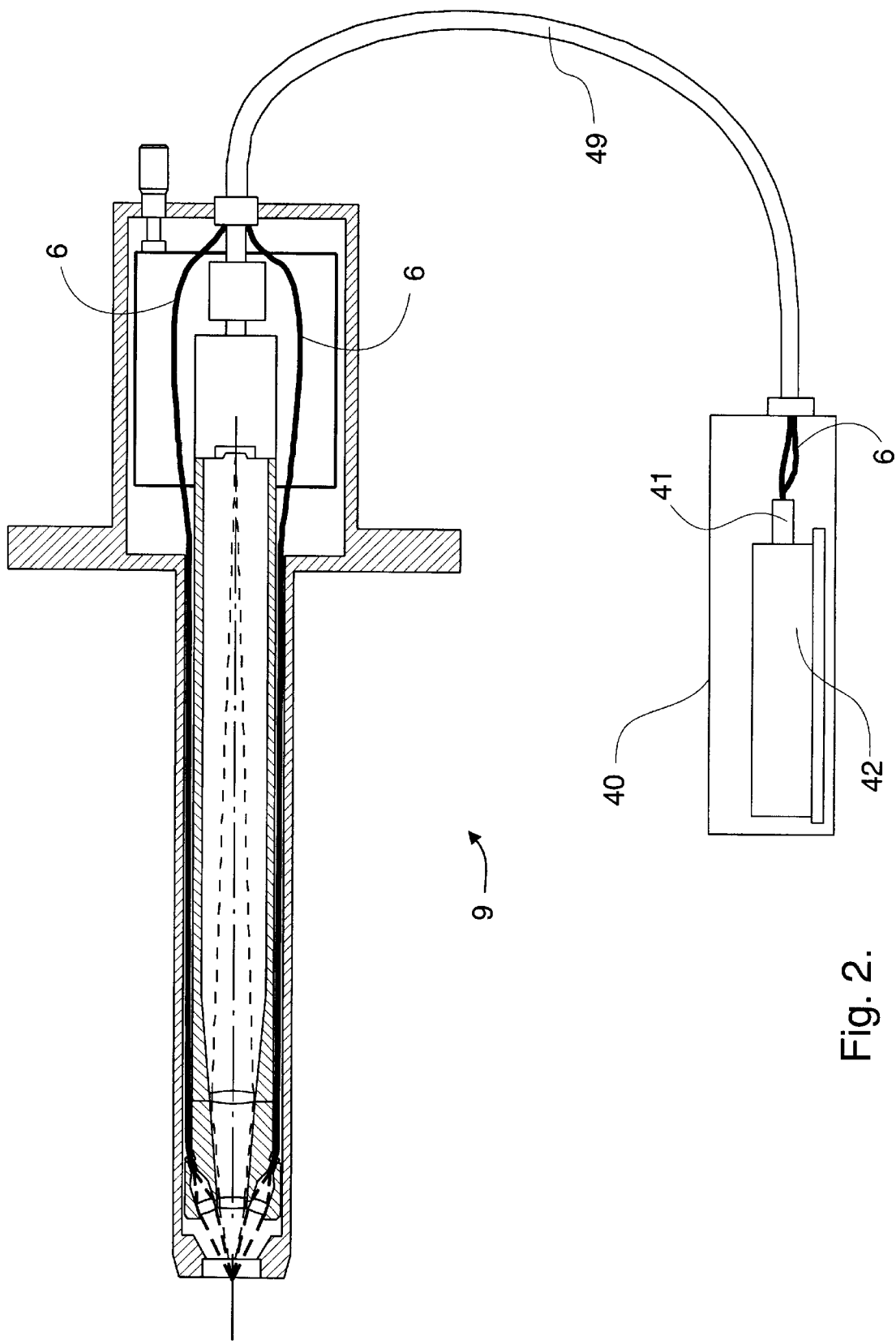
FIG. 2 shows the probe with an external light source.

FIG. 2 shows another embodiment which uses a high-power laser 42 instead of a laser diode as a light source. The laser 42 is housed in the control unit 40, which also contains the power supply and control circuitry for the laser. The light from the laser is launched into optical fibers 6 by the coupler/distributor 41. The light is carried into the probe assembly by the fibers 6 contained in the cable 49. The fibers 6 then carry the light to the illumination control system as in the previous embodiment. The external laser 42 is more expensive, but allows selection of other wavelengths of light for applications which are highly absorbing of typical laser diode wavelengths.

It should be noted that it is theoretically possible to use a white light source, but typical white light stroboscopic sources, such as gas-discharge flash tubes and arc lamps, have a large emitting area and are non-directional. This would require an elaborate optical system for condensing and focusing the energy from a large light source into a relatively small fiber. Another disadvantage of these types of lamps is that they have a very short lifetime, about 10 pulses, which is only about one month at 30 pulses per second.

Figure 3:
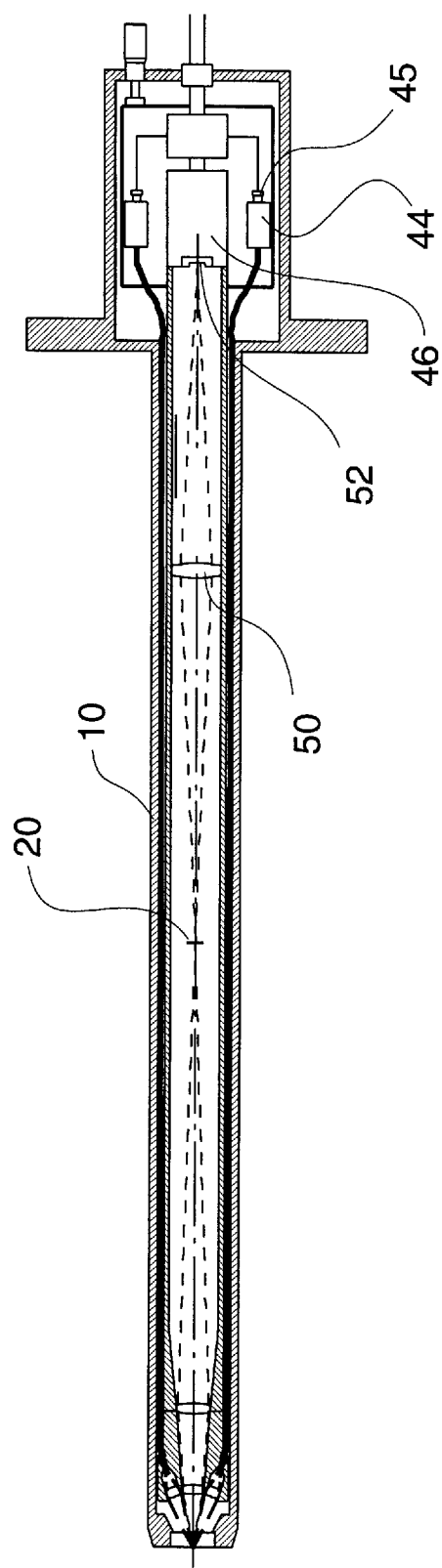
FIG. 3 is a cross section of the probe showing a method to lengthen the optical assembly without degrading the image quality.

FIG. 3 shows how the length of the probe tube 10 can be extended by using relay optics. Lens 50 is a conjugate ratio relay lens, and by placing it between the original image plane 20 and the image detector 52, the probe can be lengthened by 4 times the focal length of lens 50. Additional relay lenses may be added to further lengthen the probe. The optical fibers 6 and all of the structural components are lengthened to match the imaging optics.

By adding length to the probe, the image detector, image electronics, and the lasers can all be isolated further from the temperature conditions of the process slurry. In some applications it may be required to have a longer probe in order to reach a representative area inside of a process vessel. The ability to lengthen the optical assembly without degrading the image quality is an advantage of the present invention over devices using tapered optical fibers such as the apparatus shown in U.S. Pat. No. 5,191,388.

Figure 4:
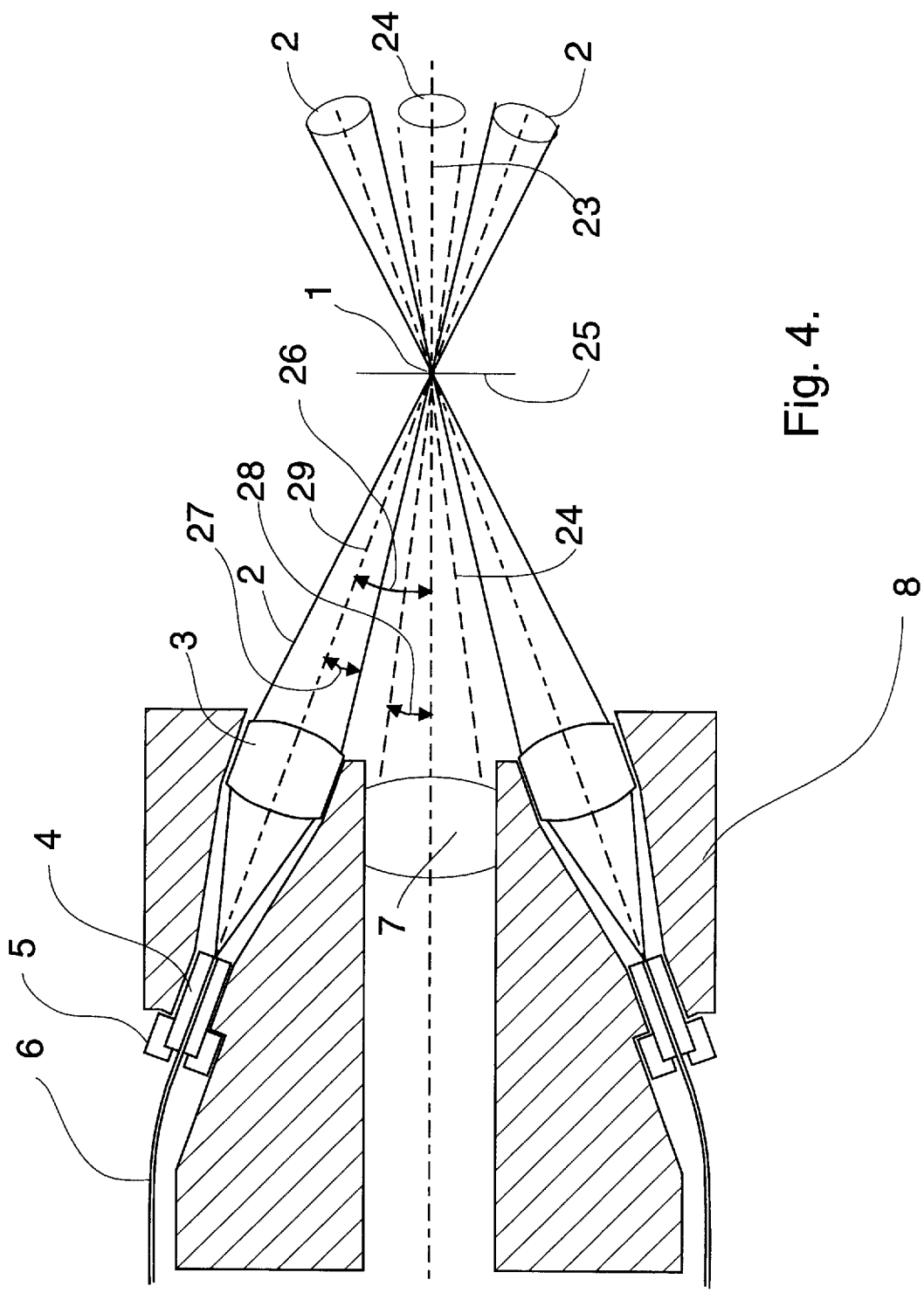
FIG. 4 is a cross section of the probe tip, showing the field of view and the illumination beams.

The relationship of the illumination components to the imaging optic is shown in cross section in FIG. 4. There are three angles noted in the drawing; 1) the half-angle 28 of the field of view 24, 2) the angle 26 between the illuminating beam axis 29 and the optical system axis 23, and 3) the half-angle 27 of the focused illuminating beam 2. In order to illuminate only the area of the field of view 24 in the focal plane 25, angle 26 must be greater than the sum of half-angle 27 and half-angle 28. This arrangement ensures that the illuminating beam 2 does not overlap the field of view 24 at any other point except at the focal plane 25. The optics of the illumination system must be chosen carefully so that the size of the focal spot 1 of the illumination beam 2 closely matches the size of the field of view 24 at the focal plane 25. The illumination system must have as large a numerical aperture as possible to create a short beam waist at the focal spot 1 in order to maximize the light intensity at the focal plane. At the same time the numerical aperture must be small enough to prevent light from the illumination beam 2 from crossing into the field of view 24 at any point other than the focal plane 25, to prevent multiple scattering of light from particles outside of the focal area.

Note that focal plane 25 is positioned just at or very near to the outside surface of the probe window (reference numeral 11 in FIG. 1). The window 11, while functioning to isolate the process slurry from the optics, is also critical to the optical performance of the system. By placing the focal plane at or near the window surface, the illuminating light and the backscattered light from the particles does not travel a long distance through the slurry, and therefore is not degraded by particles in between the window and the focal plane. The arrangement allows the invention to acquire excellent images even at high concentrations of particles.

The configuration and has the further advantage of creating no direct reflections from the light source into the imaging optical system, because the illuminating beam angles are carefully controlled.

Another advantage of this illumination arrangement is explained by the well known nature of light scattering by particles, explained by Mie scattering theory. Much more light is scattered in the forward direction by small particles than back toward the source, often by orders of magnitude (Kerker). Using an unfocused beam, such as in the previous devices, means that the particles behind the image plane are illuminated by the forward scattered component of the light. These illuminated particles increase the background light level, reducing the contrast of the image of particles in the image plane. By illuminating the particles from an angle 26 to the viewing axis, the light that is scattered forward does not enter the field of view, and only particles in the area of interest are illuminated.

Figure 5:
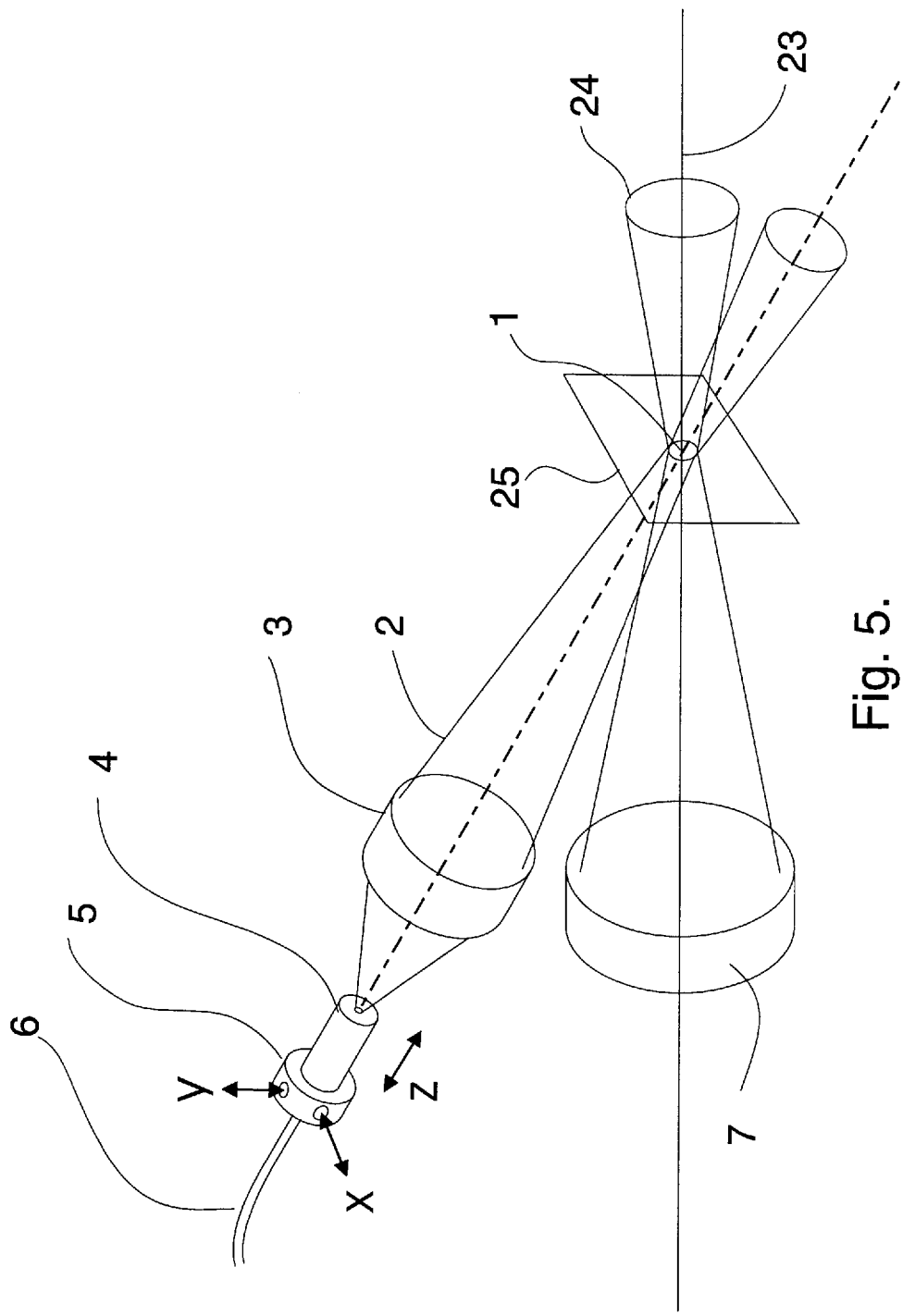
FIG. 5 shows a detail of the illumination control system.

The illumination system is adjusted as shown in FIG. 5. The light emitted from the end of the fiber 6 is collected by lens 3, which focuses the light, forming beam 2. Beam 2 is focused to its smallest point at focal spot 1. The position of the focal spot 1 is adjusted by moving the ferrule 4 with x-y adjusting means 5. The distance to the focal spot is adjusted by moving the ferrule along its z-axis, relative to the lens 3. The position of the focal spot 1 is adjusted to coincide with the area of the focal plane 25 of the imaging optic which is in the field of view 24.

Using this method, the focal spots of multiple beams which are radially positioned around the imaging optic may be focused upon the same focal area. Particles can therefore be illuminated from all sides simultaneously, or can be illuminated from selected angles depending on the number of light sources used.

FIG. 6 compares the radiant incidence, or light intensity, for different illumination systems as a function of distance from the image plane $d_0$ along the optical axis. FIG. 6A shows the end of a fiber bundle 70, like that used in U.S. Pat. No. 5,191,388, and is representative of the previous systems which use unfocused illumination. Light is emitted from the bundle according to the numerical aperture of the fibers, forming a light cone 71 with a diverging angle. In this type of system the field of view is the same as the light cone. Since this system has no focal point, but images directly at the surface of the fiber ends, then image plane do is adjacent to the end of the bundle. FIG. 6B shows the decrease in the radiant incidence I along the optical axis 75 as the distance d from the image plane increases. Note that there is still a significant amount of light intensity even at large distances from the image plane $d_0$. Particles which are in the field of view, even though not in the image plane, will scatter this light, causing unfocused images, and interference with the light scattered from particles in the image plane.

Figure 6A:
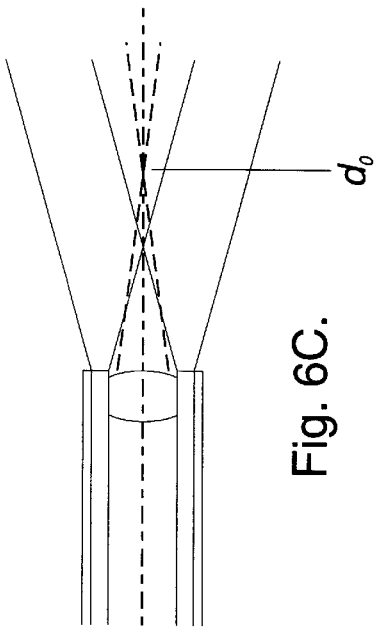
FIGS. 6A–6F illustrates the intensity along the optical axis for different illumination systems.
Figure 6B:
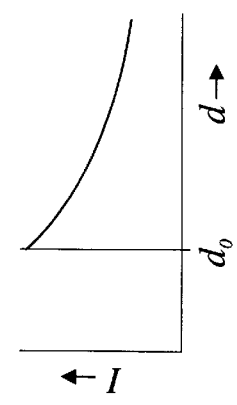
Figure 6C:
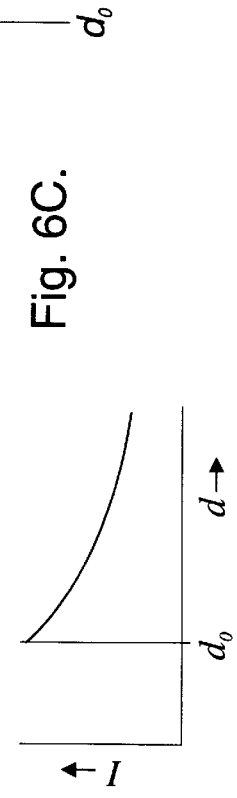
Figure 6D:
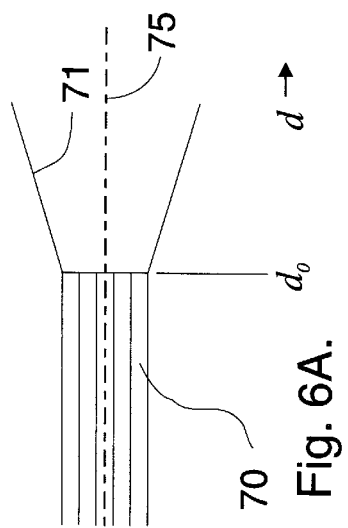

FIG. 6C shows a device using optical fibers 76 arranged concentrically around the viewing optic 77, which is a conventional method of illumination in borescopes. The light cones 79 created by the individual fibers overlap to form a central light cone 80. As can be seen in FIG. 6D, the intensity is actually greatest at some point in between the viewing optic the image plane do, then the intensity decreases as distance d increases. As in the previous example, there is a great deal of light in the field of view 78 of the viewing optic 77, which can be scattered by out-of-focus particles.

Figure 6E:
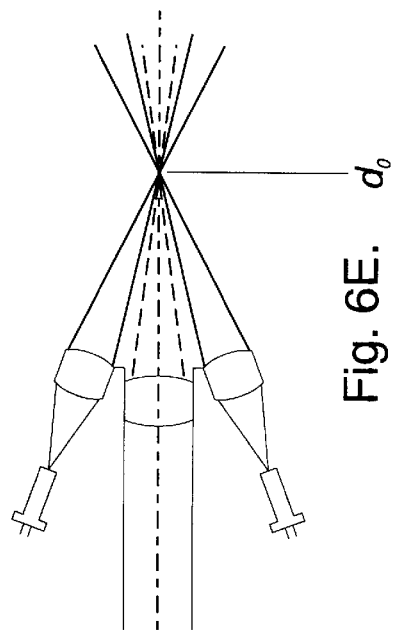
Figure 6F:
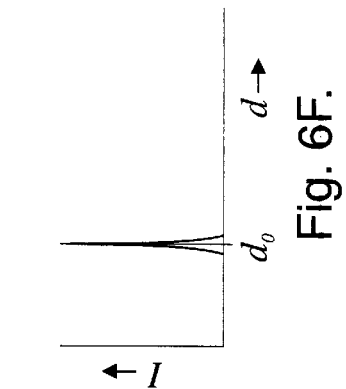

The illumination system of the present invention is shown in FIG. 6E. The illumination beam 2 is focused by lens 3 to an area which coincides with both the image plane $d_0$ and field of view 81 of the imaging optic 7. With this configuration, the light is not spread over a large area of the field of view, and as shown in FIG. 6F, the intensity of the illuminating beam is concentrated at $d_0$, decreasing to zero at a very short distance from the image plane. This means that particles that are not in focus will not be illuminated, increasing the contrast of the images of particles in the image plane.

FIG. 7 shows why the probe must be positioned carefully for the best material presentation to the window. The probe 10 with window 11 is placed into a moving slurry flow 13. In FIG. 7A, window 11 is mounted flush with the wall of the pipeline or vessel. The friction at the wall 16 of causes the velocity V of the stream closer to the wall to be slower than near the center of the flow stream. Very near to the wall, a thin layer of material 15 moves very slowly, which is the reason deposits may form on the insides of pipelines even when carrying high flow rates. Particles and droplets 17, being carried by the higher flow velocities, do not readily enter the slow layer 15, and thus are prevented from getting close to a window which is mounted flush to the wall 16. FIG. 7B shows the probe inserted further with the window parallel to the flow. In this case the probe creates an obstruction at right angles to the flow, causing a shock wave 18 which deflects the flow away from the window, causing a dead zone 12 in front of the window.

In FIG. 7D, the flow against the blunt end of the probe also forms a shock wave, around which most of the material flows, and between this shock wave and the window there is a dead zone 12, into which material does not readily flow. The low velocity at the window in case 7a, and the dead zone 12 in cases 7b and 7d prevent representative measurement of the particles in the flow stream 13, and allow deposits to form on the window.

Only in FIG. 7C is there an impinging flow 14 against and across the window surface, with the flow carrying the particles close to the window for the best measurement presentation, as well as creating a scraping action which helps to prevent build-up on the window. The best orientation is when the angle of the window to the flow is about 45°.

Figure 8:
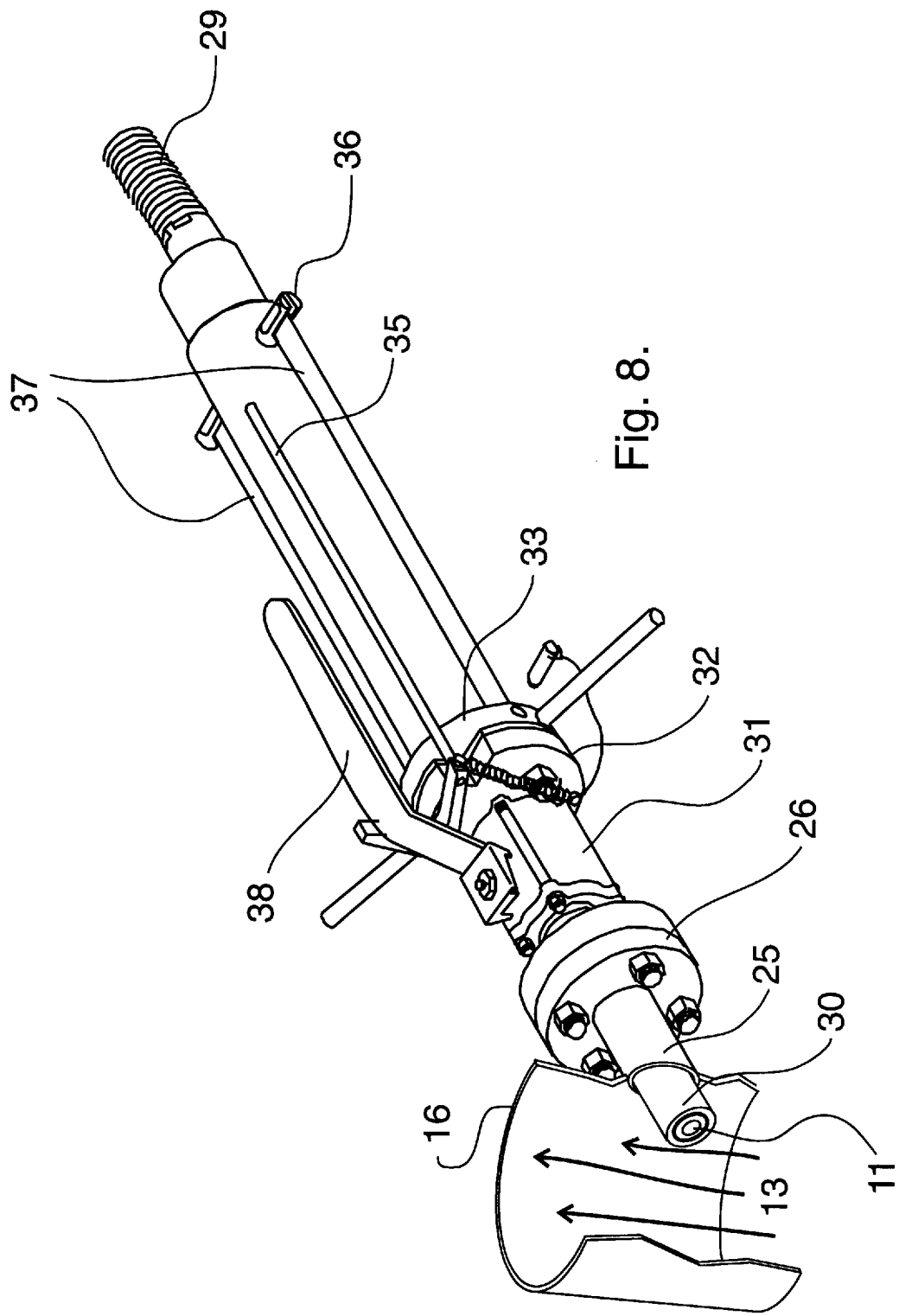
FIG. 8 shows a ball valve and gland system which allows the insertion or removal of a probe into a pipe or vessel while the slurry is flowing.
Figure 9:
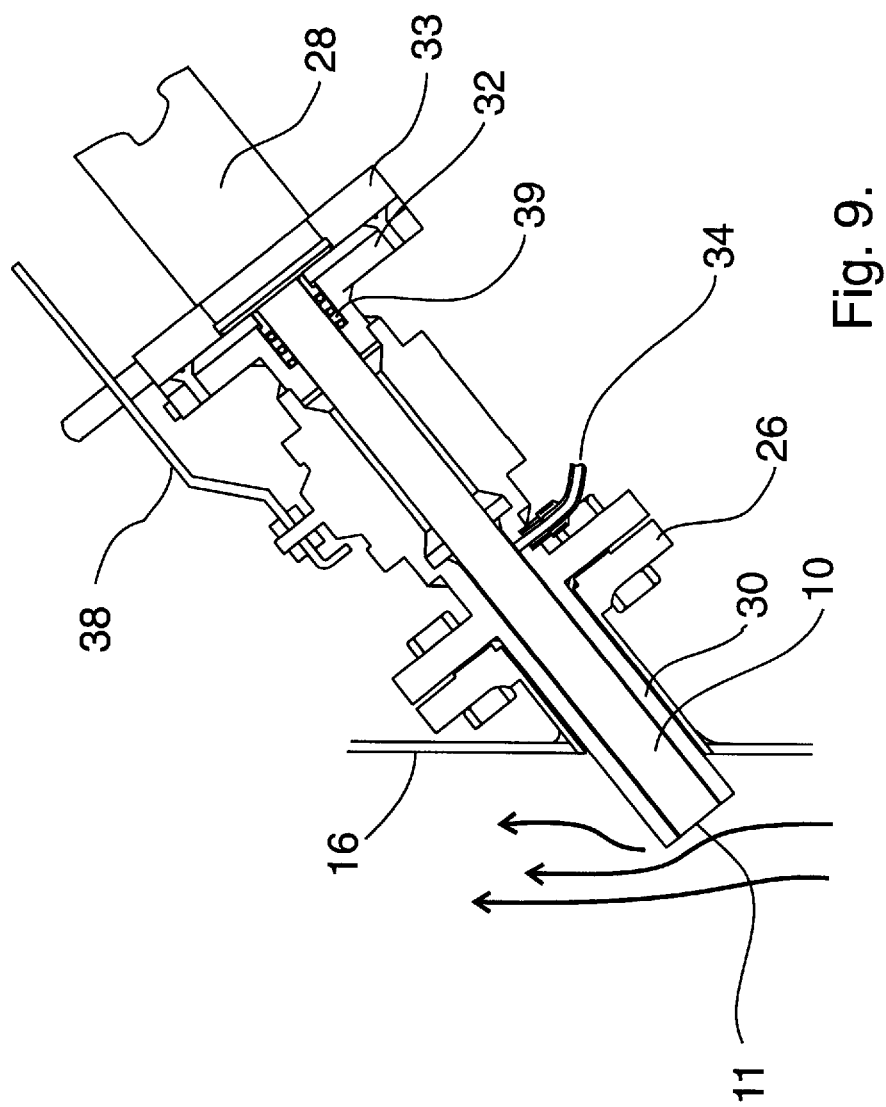
FIG. 9 shows a cross section of the ball valve/insertion assembly.

To avoid the condition shown in FIG. 7A, it is necessary to insert the probe tip deep enough into the flowing material to eliminate the wall effects. FIGS. 8 and 9 show an in-line installation which positions the probe window away from the pipe wall and at the proper angle to the flow. It has the further advantage of allowing the probe to be inserted or removed while the process is in operation, without having to shut down the process and drain the pipeline. FIG. 9 shows the cross section of the assembly. The tubular probe tube 10 of the probe assembly is inserted through the assembly formed by gland seal 39, flange 32, ball valve 31, probe shield 30, flange 26 and pipe section 25, with the probe window 11 in direct contact with the slurry flow 13. The pipe section 25 is welded at an angle (angle A in FIG. 7C) to the wall 16 of a pipeline or process vessel. The probe shield 30 extends to the tip of the probe but does not obstruct the flow, and is used to protect the probe tube 10 against excessive wear in abrasive slurries. The ball valve allows the probe to be inserted into (or extracted from) a continuously operating process. Referring to FIG. 8, locking collar 33 is attached to probe housing 28 and is used to lock the probe body to flange 32. O-ring assembly 39 provides a pressure seal, and all parts are built to withstand high process pressures. The probe is extracted by unlocking collar 33, sliding the probe assembly and locking collar along the two guide bars 37, past interlock bar 35 until collar 33 hits against toggle bolt assembly 36. The ball valve can then be closed by rotating handle 38 through 90°, isolating the process. The toggle bolts are then removed to allow the probe to be fully extracted. The probe is reinstalled following these procedures in reverse. With the ball valve closed, the end tip of interlock bar 35 determines the maximum insertion distance of collar 33 to prevent the probe window from touching the closed ball of the valve assembly. When the ball valve handle 38 is opened, interlock bar 35 is moved out of the way, allowing collar 33 to slide back into its lockable position against the gland seal 39. The probe body and all wetted parts of the ball valve assembly are made of materials which are suited to be compatible with the materials and environmental conditions of the process slurry. In some crystallization applications, the volume between the probe tube 10 and the probe shield 30 may cake up with crystallized material. When this happens it may be very difficult to remove the probe assembly without first dissolving the hardened material using a flow of heated suspension liquid. This can be done on a continuous basis by adding a pressurized flow of suspension liquor injected into the probe shield through the fitting 34 at the side of the ball valve assembly. In a crystallization process, heating the injected suspension liquid to a temperature at least 10° C. above that of the probe will eliminate crystallized solids build-up at the probe.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An apparatus for providing an image of a fluid medium, the apparatus comprising:
   a probe for insertion into said fluid medium, said probe including a window at the tip of said probe, and said probe adapted for placement in said fluid medium such that said window is disposed at an insertion angle to a direction of flow of said fluid medium;
   a light source for generating an illuminating light;
   a light transmission system for transmitting said illuminating light from said light source to said window, said light transmission system including focusing lens means for focusing said illuminating light onto a focal plane in said fluid medium;
   an image detector;
   a processor; and
   an optical system for collecting backscattered light from said fluid medium over a collection angle to form an optical image of said fluid medium, said optical system having a focal plane substantially the same as the focal plane of said illuminating light, wherein said optical system using said light transmission system for relaying the optical image to said image detector and said processor such that said image detector and said processor are operative to generate said image.

2. The apparatus of claim 1, wherein the probe includes means to move the focal plane of said image acquiring means relative to the surface of the window, without changing the focal length or magnification of the optical system and keeping the spatial relationship between the illumination system and the optical system constant.

3. The apparatus of claim 1, where said light source consists of a pulsed laser diode.

4. The apparatus of claim 1, where said optical system for collecting the backscattered light includes a magnifying lens system.

5. The apparatus of claim 1, where the light transmitting system is a fiber optic cable and said light transmitting system includes focusing optics to focus the illuminating light from said light source into one end of a fiber optic cable.

6. The apparatus of claim 1, where said optical system for collecting said backscattered light consists of an imaging lens.

7. The apparatus of claim 1, where the probe is adapted to have an insertion angle between 30° to 45°.

8. The apparatus of claim 1, where the backscattered light goes through an optical shutter, said optical shutter only open for the duration of the illuminating light.

9. An apparatus for providing an image of a fluid medium, the apparatus comprising:
   a probe for insertion into said fluid medium, said probe including a window at the tip of said probe, and said probe adapted for placement in said fluid medium such that said window is disposed at an insertion angle to a direction of flow of said fluid medium;
   a light source for generating an illuminating light;
   a light transmission system for transmitting said illuminating light from said light source to said window, said light transmission system including focusing lens means for focusing said illuminating light onto a focal plane in said fluid medium;
   a CCD array;
   a processor; and
   an optical system for collecting backscattered light from said fluid medium over a collection angle to form an optical image of said fluid medium, said optical system having a focal plane substantially the same as the focal plane of said illuminating light, wherein said optical system using said light transmission system for relaying the optical image to said CCD detector and said processor such that said CCD array and said processor are operative to generate said image.

10. The apparatus of claim 9, where said CCD array includes a storage array for storing said optical image and for allowing short exposure integration times.

11. A method of generating an optical image of a fluid medium, the method comprising the steps of:

inserting a probe into said fluid medium, said probe including a window at the tip of said probe, said probe inserted at an insertion angle to a direction of flow of said fluid medium;

generating an illuminating light;

transmitting and focusing said illuminating light through the window into said fluid medium such that said illuminating light is focused at a focal plane onto said fluid medium;

collecting backscattered light over a collection angle from said fluid medium using a set of collection optics;

focusing said backscattered light from said focal plane onto an image detector to form said optical image of said fluid medium on said image detector; and relaying said optical image to an image processor.

* * * * *